United States Patent [19]

Inoki et al.

[11] Patent Number: 5,510,511
[45] Date of Patent: Apr. 23, 1996

[54] PROCESS FOR PREPARING N,O-DIALKYLHYDROXYLAMINE, ITS SALTS OR INTERMEDIATES IN THEIR SYNTHESIS

[75] Inventors: Satoshi Inoki; Mitsuyuki Takesue; Isao Hashimoto; Noriaki Kihara; Kiyoaki Sugi, all of Kuga, Japan

[73] Assignee: Mitsui Petrochemical Industries, Ltd., Tokyo, Japan

[21] Appl. No.: 97,225

[22] Filed: Jul. 27, 1993

[30] Foreign Application Priority Data

| Jul. 31, 1992 | [JP] | Japan | 4-205804 |
| Oct. 14, 1992 | [JP] | Japan | 4-276381 |
| Oct. 23, 1992 | [JP] | Japan | 4-286283 |
| Mar. 26, 1993 | [JP] | Japan | 5-068664 |
| Jun. 30, 1993 | [JP] | Japan | 5-162981 |

[51] Int. Cl.$^6$ ............................................. C07C 261/00
[52] U.S. Cl. ................................. 560/157; 564/301
[58] Field of Search ................................ 560/160, 157

[56] References Cited

U.S. PATENT DOCUMENTS

| 3,230,260 | 1/1966 | Snyder . | |
| 4,469,884 | 9/1984 | Reissenweber et al. . | |
| 4,914,124 | 4/1990 | Müller | 514/478 |
| 5,315,032 | 5/1994 | Nishihira | 560/157 |

FOREIGN PATENT DOCUMENTS

| 0449558 | 2/1991 | European Pat. Off. . |
| 1377470 | 9/1963 | France . |
| 3245503A1 | 9/1982 | Germany . |
| 3245503 | 6/1984 | Germany . |
| 1042191 | 9/1966 | United Kingdom . |

OTHER PUBLICATIONS

Tetrahedron Letters, vol. 30, No. 1, 1989, pp. 31–34, R. Sulsky, et al.

Chemical Abstracts vol. 81, 1974, Columbus, Ohio, abs. No. 151392c, & Farmaco, Ed. Sci. vol. 29, No. 9, 1974, pp. 710–719, B. Cavalleri, et al.

Organic Preparations and Procedures International (OPPI) vol. 19, No. 1, Feb., 1987, pp. 75–78.

Tetrahedron Letters, vol. 24, No. 3, pp. 231–232, Harris and Wilson, "Synthesis of tert–Butyl Aminocarbonate . . . ". (1983).

Primary Examiner—Michael L. Shippen
Attorney, Agent, or Firm—Sherman and Shalloway

[57] ABSTRACT

A process for preparing N,O-dialkylhydroxycarbamic acid ester which comprises reacting hydroxylamine or its salt with dihydrocarbyl carbonate in the presence of a basic compound to prepare hydroxycarbamic acid ester and subsequently alkylating this compound with an alkylating agent; a process for recovering N,O-dialkylhydroxycarbamic acid ester which comprises azeotropically distilling the ester with water from a solution containing the ester; a process for preparing N,O-dialkylhydroxylamine which comprises hydrolyzing N,O-dialkylhydroxycarbamic acid ester in an aqueous solution or a hydrous solvent in the presence of an alkali; a process for purifying N,O-dialkylhydroxylamine hydrochloride which comprises adding aldehyde or ketone to a solution of N,O-dialkylhydroxylamine hydrochloride containing O-alkylhydroxylamine hydrochloride as impurities to convert the O-alkylhydroxylamine hydrochloride into O-alkyl aldoxime or O-alkyl ketoxime and subsequently separating the N,O-dialkylhydroxylamine hydrochloride from the reaction system; and a process for separating N,O-dialkylhydroxylamine hydrochloride which comprises (i) adding benzene or alkylated benzene to an aqueous solution containing N,O-dialkylhydroxylamine hydrochloride, azeotropically removing water or a hydrochloride solution, and, subsequently (ii)adding alcohol thereto to obtain N,O-dialkylhydroxylamine hydrochloride in the form of crystal.

13 Claims, No Drawings

PROCESS FOR PREPARING N,O-DIALKYLHYDROXYLAMINE, ITS SALTS OR INTERMEDIATES IN THEIR SYNTHESIS

This invention relates to the improvements in process for preparing N,O-dialkylhydroxylamine such as N,O-dimethylhydroxylamine or the like as an intermediate in the synthesis of pharmaceuticals and agricultural chemicals, its salts and N,O-dialkylhydroxycarbamic acid ester as an intermediate in their synthesis.

BACKGROUND OF THE INVENTION

As a process for preparing N,O-dialkylhydroxycarbamic acid ester from hydroxylamine or its salts, a process comprising reacting chloroformic acid ester with a salt of hydroxylamine in the presence of sodium hydroxide and subsequently reacting the reaction solution with dialkyl sulfate in the presence of sodium hydroxide is known generally.

For example, a process disclosed in Org. Prep. Proced. [Vol. 19, P. 75 (1987)] is known as a process for preparing ethyl N,O-dimethylhydroxycarbamate. According to this process, hydrochloride of hydroxylamine is reacted with ethyl chloroformate using a sodium hydroxide solution to obtain ethyl hydroxycarbamate, and then dimethylating this product with dimethyl sulfate and a sodium hydroxide solution to obtain ethyl N,O-dimethylhydroxycarbamate in a 70–73% yield.

With respect to butyl N,O-dimethylcarbamate, a process disclosed in the specification of West German Patent Application Laid-open No. 3,245,503 is known. This process comprises reacting sulfate of hydroxylamine as a starting material with butyl chloroformate in the presence of sodium hydroxide, extracting the reaction product with dichloromethane, drying the extract, distilling the solvent away from the dried extract to obtain butyl hydroxycarbamate and dimethylating this product using dimethyl sulfate and a sodium hydroxide solution to obtain ethyl N,O-dimethylhydroxycarbamate in the total yield of 65%.

However, the processes which had been reported so far was disadvantageous in that they give the aimed N,O-dialkylhydroxycarbamic acid ester in low yields in order to perform industrially. In addition, the above processes, according to the study by the present inventors, have been found to be disadvantageous in the case of carbamoylating hydroxylamine or its salt with methyl chloroformate and then dialkylating the resulting product to prepare N,O-dialkylhydroxycarbamate in that methyl chloroformate to be used as a carbamoylating agent is liable to be hydrolyzed because this reaction is carried out using an aqueous solution as a solvent and the yield of the aimed product becomes further low because a hydroxyl group of methyl hydroxycarbamate as the formed intermediate reacts with methyl chloroformate, as will be mentioned in Referential Example 1.

Furthermore, as a process for preparing N,O-dimethylhydroxylamine, for example, a process comprising obtaining the same through sulfonimide which is obtained by reacting nitrite, hydrogensulfite and SO2, as is disclosed in the specification of French Patent Application Laid-open No. 1,377,470, or the like is generally known. However, this process is disadvantageous for an industrial process because a large quantity of waste fluid is brought about.

As a method for recovering N,O-dimethylhydroxycarbamic acid ester, a method comprising extracting N,O-dimethylhydroxycarbamic acid ester with an organic solvent such as halogenated hydrocarbon or the like can be enumerated. From the viewpoint of environmental problems, however, a more effective method is desired. In addition, because O-methylhydroxylcarbamic acid ester, which is formed as impurities in the course of the formation reaction of N,O-dimethylhydroxycarbamic acid ester, is also extracted, O-methylhydroxyamine is contained in N,O-dimethylhydroxylamine obtained after deprotection. Boiling points of these compounds are so close as 42.3° C. for N,O-dimethylhydroxylamine and 48.1° C. for O-methylhydroxylamine, so that it is very difficult to purify the same by distillation and a multi-stage distillation column is required for separation.

As a method for purifying N,O-dimethylhydroxylamine, the specification of U.S. Pat. No. 3,230,260 discloses a method for removing O-methylhydroxylamine which comprises reacting O-methylhydroxylamine contained in N,O-dimethylhydroxylamine with formaldehyde at a pH 7 or lower to prepare gaseous O-methylformaldehyde oxime and removing it.

In order to remove O-methylhydroxylamine according to the method disclosed in the specification of U.S. Pat. No. 3,230,260, such complicated steps as once extracting N,O-dimethylhydroxycarbamic acid ester as an intermediate and a reaction product, e.g., O-methylhydroxycarbamic acid ester from an aqueous solution containing inorganic salts and the like using an organic solvent such as halogenated hydrocarbon or the like, carrying out deprotection after concentrating the extracted solvent, reacting the resulting solution with formaldehyde to prepare gaseous O-methylformaldehyde oxime and separating this must be gone through. In addition, a halogenated hydrocarbon solvent to be used in the extraction step and formaldehyde to be used in the reaction are both highly toxic. Particularly, formaldehyde has such low legal permissible concentration as 2 ppm and thus is a substance very difficult to handle. Furthermore, O-methylformaldehyde oxime to be formed has a problem that, because its boiling point is as low as −12° C., an apparatus having high cooling efficiency is necessary for its recovery and thus it will cost a great deal for an apparatus and complicated steps.

As a process for preparing N,O-dialkylhydroxylamine from N,O-dialkylhydroxycarbamic acid ester, a process of hydrolyzing the ester in the presence of hydrochloric acid as a catalyst in an aqeuous solution is generally adopted. For example, in West German Patent Application Laid-open No. 3,245,503, butyl N,O-dimethylhydroxycarbamate was hydrolyzed with hydrochloric acid, concentrated and evaporated to dryness to obtain N,O-dimethylhydroxylamine hydrochloride. In Org. Prep. Proced.[Vol. 19, P. 75 (1987)], ethyl N,O-dimethylhydroxycarbamate as hydrolyzed with hydrochloric acid and the hydrolysate was azeotropically dehydrated using isopropanol to obtain N,O-dimethylhydroxylamine hydrochloride. However, these process, because of using an acid as a catalyst, require a hydrochloric catalyst beyond stoichiometry in order that the formed N,O-dimethylhydroxylamine forms a salt with hydrochloric acid. In addition, in order to recover the obtained N,O-dimethylhydroxylamine hydrochloride in an anhydrous state, such complicated post-treatment as disclosed in Org. Prep. Proced. [Vol. 19, P. 75 (1987)] is required. Therefore, these cannot be industrial processes for preparation. Furthermore, in case of aiming to obtain free N,O-dimethylhydroxylamine, alkali equivalent or more to hydrochloric acid used is required for neutralization and thus the process comes to bring out a great deal of waste fluid. Incidentally, although there can be a process using sulfuric acid as a catalyst instead of hydrochloric acid, side-reaction takes place to lower the purity of N,O-dimethylhydroxylamine (see Comparative Example 2).

Generally, N,O-dialkylhydroxylamine can be obtained according to a process comprising using hydroxylamine as a starting material, converting the same into hydroxycarbamic acid ester and dialkylating or deprotecting the ester; a process comprising using nitrite as a starting material, reacting hydrogensulfite with SO2 and, according to demand, repeating alkylation and hydrolysis; etc. According to these processes, however, O-alkylhydroxylamine is contained in the obtained N,O-dialkylhydroxylamine as impurities, so that it become necessary to remove O-alkylhydroxylamine from N,O-dialkylhydroxylamine. In this respect, there is a description about it in the specification of U.S. Pat. No. 3,230,260 as aforementioned, and it has the aforementioned problems.

With respect to a method for separating N,O-dimethylhydroxylamine hydrochloride, the following two methods have been reported so far.

One is a method disclosed in the specification of West German Patent Application Laid-open No. 3,245,503, according to which a solution of N,O-dimethylhydroxylamine obtained by hydrolyzing butyl N,O-dimethylhydroxycarbamate with concentrated hydrochloric acid was evaporated to dryness to quantitatively obtain hydrochloride of N,O-dimethylhydroxylamine.

The other is a method disclosed in Org. Prep. Proced. [Vol. 19, P. 75 (1987)], which comprises decomposing ethyl N,O-dimethylhydroxycarbamate with concentrated hydrochloric acid, removing most of water using a rotary evaporator, performing azeotropic dehydration by adding 2-propanol to the resulting product in order to remove moisture completely, repeating this operation 6 times, filtering crystals after adding 2-propanol to the dehydrate, drying the crystals, thereby obtaining hydrochloride of N,O-dimethylhydroxylamine in a 93–95% yield.

However, the present inventors supplementarily examined the method of evaporation to dryness disclosed in the specification of West German Patent Application Laid-open No. 3,245,503. In this supplementary examination, the solvent was distilled away using a rotary evaporator at a bath temperature of 60° C. under a pressure of 40 mmHg and the resulting product was further dried at room temperature at a pressure of 1 mmHg for 10 hours. As the result, it was found that the moisture content of the obtained crystal was 11% and thus it was difficult to completely remove moisture in the crystal. In addition, it is difficult to take out the crystal obtained by evaporation to dryness from a container use for drying, so that it is difficult to perform this method industrially.

On the other hand, as a result of supplementarily examining the method disclosed in Org. Prep. Proced. [Vol. 19, P. Y5 (1987)], the present inventors confirmed that N,O-dimethylhydroxylamine hydrochloride could be obtained in the yield given in the above literature. However, not only because the procedures of this method is very complicated but also because 2-propanol forms an azeotrope with water and is miscible with water, the recovery of a solvent used becomes low. Accordingly, it is difficult to perform this method industrially from the viewpoint of economy.

It is the first object of the present invention to provide a process for preparing N,O-dialkylhydroxycarbamic acid ester in yields higher than the conventional processes.

It is the second object of the present invention to provide a process for recovering N,O-dialkylhydroxycarbamic acid ester as an intermediate of N,O-dialkylhydroxylamine selectively, more readily and safely than the conventional processes to obtain N,O-dialkylhydroxylamine as the final aimed product.

It is the third object of the present invention to provide a process for industrially advantageous preparation of N,O-dialkylhydroxylamine which comprises hydrolyzing N,O-dialkylhydroxycarbamic acid ester by using an alkali to form N,O-dialkylhydroxylamine without forming its salt.

It is the fourth object of the present invention to provide a method for removing O-alkylhydroxylamine hydrochloride contained in N,O-dialkylhydroxylamine hydrochloride, which is not only safer than the conventional methods but also enable easy recovery of O-alkyl oxime.

It is the fifth object of the present invention to provide a method for separating N,O-dialkylhydroxylamine hydrochloride, which is simpler and easier than the conventional separation methods and enables the recovery of a solvent used in high yields.

SUMMARY OF THE INVENTION

The present invention includes the following invention:

(1) A process for preparing N,O-dialkylhydroxycarbamic acid ester represented by the following formula (III)

wherein $R^1$ is a hydrocarbon group, and $R^2$ is a lower alkyl group, comprising reacting hydroxylamine represented by the formula NH2OH or its salt with dihydrocarbyl carbonate represented by the following formula (I)

wherein $R^1$ is as defined above, in the presence of a basic compound to prepare hydroxycarbamic acid ester represented by the following formula (II)

wherein $R^1$ is as defined above, and alkylating this compound with an alkylating agent in the presence of a basic compound.

(2) A process described in the above (1), wherein the dihydrocarbyl carbonate is dimethyl carbonate, the hydroxycarbamic acid ester is methyl hydroxycarbamate and the N,O-dialkylhydroxycarbamic acid ester is methyl N,O-dimethylhydroxycarbamate.

(3) A process described in the above (1), wherein the reaction temperatures in carbamoylation and dialkylation are respectively 5°±5° C. and the pHs of the reaction solutions in the reactions are respectively 12–13.

(4) A process described in the above (1), wherein the N,O-dialkylhydroxycarbamic acid ester is recovered from the obtained solution containing N,O-dialkylhydroxycarbamic acid ester by azeotropic distillation with water.

(5) A process for recovering N,O-dialkylhydroxycarbamic acid ester represented by the following formula (III)

wherein $R^1$ is a hydrocarbon group, and $R^2$ is a lower alkyl group, comprising azeotropically distilling the N,O-dialkylhydroxycarbamic acid ester(III) with water.

(6) A process described in the above (5), wherein the N,O-dialkylhydroxycarbamic acid ester is methyl N,O-dimethylhydroxycarbamate.

(7) A process for recovering N,O-dialkylhydroxycarbamic acid ester represented by the following formula (III)

$$\underset{R^2ONCOOR^1}{\overset{R^2}{|}} \quad (III)$$

wherein $R^1$ is a hydrocarbon group, and $R^2$ is a lower alkyl group, comprising azeotropically distilling the N,O-dialkylhydroxycarbamic acid ester with water from a solution containing N,O-dialkylhydroxycarbamic acid ester and O-alkylhydroxycarbamic acid ester represented by the following formula (IV)

$$R^2ONHCOOR^1 \quad (IV)$$

wherein $R^1$ and $R^2$ are as defined above.

(8) A process described in the above (7), wherein the N,O-dialkylhydroxycarbamic acid ester is methyl N,O-dimethylhydroxycarbamate.

(9) A process for preparing N,O-dialkylhydroxylamine represented by the following formula (V)

$$R^2ONHR^2 \quad (V)$$

wherein $R^2$ is as defined above, comprising hydrolyzing N,O-dialkylhydroxycarbamic acid ester represented by the following formula (III)

$$\underset{R^2ONCOOR^1}{\overset{R^2}{|}} \quad (III)$$

wherein $R^1$ is a hydrocarbon group, and $R^2$ is a lower alkyl group, in an aqueous solution or a solvent containing water in the presence of an alkali.

(10) A process described in the above (9), wherein the N,O-dialkylhydroxycarbamic acid ester is methyl N,O-dimethylhydroxycarbamate and the N,O-dialkylhydroxylamine is N,O-dimethylhydroxylamine.

(11) A process described in the above (9), wherein the alkali to be used for hydrolysis is a hydroxide or a carbonate of an alkali metal.

(12) A process for purifying N,O-dialkylhydroxylamine hydrochloride, comprising adding an aldehyde or a ketone of $C_2$-$C_8$ to an N,O-dialkylhydroxylamine hydrochloride solution containing O-alkylhydroxylamine hydrochloride as impurities to convert the O-alkylhydroxylamine hydrochloride into O-alkyl aldoxime or O-alkyl ketoxime and subsequently separating the N,O-dialkylhydroxylamine hydrochloride from the reaction system.

(13) A process described in the above (12), wherein the N,O-dialkylhydroxylamine hydrochloride is N,O-dimethylhydroxylamine hydrochloride.

(14) A process for separating N,O-dialkylhydroxylamine hydrochloride, comprising
   (i) adding benzene or alkylated benzene to an aqueous solution containing N,O-dialkylhydroxylamine hydrochloride, azeotropically removing water or a hydrochloric acid solution and, subsequently
   (ii) adding alcohol thereto to obtain N,O-dialkylhydroxylamine hydrochloride in the form of crystal.

(15) A process described in the above (14), wherein the N,O-dialkylhydroxylamine hydrochloride is N,O-dimethylhydroxylamine hydrochloride.

(16) A process described in the above (14) or (15), wherein the alkylated benzene is a benzene substituted by 1 to 3 alkyl groups having 1 to 3 carbon atoms.

(17) A process described in any of the above (14)–(16), wherein the alcohol is an alcohol of $C_1$-$C_6$.

DETAILED DESCRIPTION OF THE INVENTION

As examples of the hydrocarbon group represented by $R^1$ in the above formula (I)–(IV), alkyl groups of $C_1$–$C_5$ such as a methyl group, an ethyl group, a n-propyl group, an isopropyl group, a n-butyl group, an isobutyl group, a sec-butyl group, a tert-butyl group, a n-pentyl group, etc., preferably, alkyl groups of $C_1$–$C_3$ such as a methyl group, an ethyl group, a n-propyl group, an isopropyl group, etc.; cycloalkyl groups of $C_3$–$C_7$ such as a cyclopropyl group, a cyclobutyl group, a cyclopentyl group, a cyclohexyl group, a cycloheptyl group, etc.; aryl groups such as a phenyl group, a tolyl group, a xylyl group, etc.; and, aralkyl groups such as a benzyl group, a phenethyl group, etc. can be enumerated.

The lower alkyl groups represented by $R^2$ in the above formula (III)–(V) means alkyl groups of $C_1$–$C_4$. As examples thereof, a methyl group, an ethyl group, a n-propyl group, an isopropyl group, a n-butyl group, an isobutyl group, a sec-butyl group and tert-butyl group can be enumerated.

Firstly, the present process for preparing N,O-dialkylhydroxycarbamic acid ester will be detailed.

As examples of hydroxylamine or its salt to be used as a starting material, hydroxylamine, hydroxylamine sulfate, hydroxylamine hydrochloride can be enumerated, among which hydroxylamine sulfate and hydroxylamine hydrochloride are particularly preferable from the viewpoint of stability and price. These hydroxylamine or its salt may be in the state of an aqueous solution or an organic solution such as methanol or the like.

As examples of dihydrocarbyl carbonate (I), dialkyl carbonates such as dimethyl carbonate, diethyl carbonate, n-propyl carbonate, diisopropyl carbonate, etc.; dicycloalkyl carbonates such as dicyclopentyl carbonate, dicyclohexyl carbonate, dicycloheptyl carbonate, etc.; diaryl carbonates such as diphenyl carbonate, ditolyl carbonate, dixylyl carbonate, etc.; and diaralkyl carbonates such as dibenzyl carbonate, diphenetyl carbonate, etc. can be enumerated. In case, for example, of preparing methyl N,O-dimethylhydroxycarbamate, dimethyl carbonate is used.

As examples of a basic compound, hydroxides of alkali metals or alkaline earth metals such as sodium hydroxide, potassium hydroxide, lithium hydroxide, cesium hydroxide and barium hydroxide; hydrogencarbonates of alkali metals such as sodium hydrogencarbonate and potassium hydrogen carbonate; carbonates of alkali metals or alkaline earth metals such as sodium carbonate, potassium carbonate, barium carbonate; and aluminate compounds such as sodium aluminate and potassium aluminate can be enumerated, which may be used independently or in combination. Among these basic compounds, sodium hydroxide is particularly preferable from the viewpoint of price. It is preferred that these basic compounds are used in the state of an aqueous solution. However, they may be used as in solid state or may be dissolved in an organic solvent such as alcohol or the like.

As examples of an alkylating agent, dialkylsulfuric acid ester such as dimethyl sulfate and diethyl sulfate; alkyl chloride such as methyl chloride, ethyl chloride, propyl chloride and butyl chloride; alkyl bromide such as methyl bromide, ethyl bromide, propyl bromide and butyl bromide; and alkyl iodide such as methyl iodide, ethyl iodide, propyl iodide and butyl iodide can be enumerated, among which dialkylsulfuric acid ester is preferable from the viewpoint of price. In case, for example, of preparing methyl N,O-dimethylhydroxycarbamate, it is preferred to use dimethyl sulfate.

As a reaction solvent, it is preferred to use water. However, inert organic solvent, for example, ethers such as diethyl ether and tetrahydrofuran; aromatic compounds such as benzene and toluene; etc. may be used independently, in combination or as a two-layer system.

The molar ratio of hydroxylamine or its salt to dihydrocarbyl carbonate (I) is generally 1/0.5–1/2, preferably 1/1–1/1.5, more preferably 1/1–1/1.3.

The molar ratio of hydroxylamine or its salt to an alkylating agent is generally 1/2 or more. In case of using dimethyl sulfate as an alkylating agent, the molar ratio is preferably 1/2–1/4, more preferably 1/2–1/2.5.

With respect to the quantity of a basic compound to be used, there is no particular restriction thereto. However, it is preferred to be used in such a quantity as control the pH of the reaction solution within the range to be described later.

Although there is no particular restriction to a method for adding a starting material, a method comprising firstly loading hydroxylamine or its salt and a reaction solvent into a reactor and subsequently supplying dihydrocarbyl carbonate (I) and a basic compound simultaneously is preferable because the reaction temperature and the pH of the reaction solution can be controlled to be constant thereby. In case of using sulfate or hydrochloride of hydroxylamine for a starting material, it is preferred to neutralize such a salt by adding a basic compound before supplying dihydrocarbyl carbonate (I).

Also in dialkylation, it is preferred to adopt a method for simultaneously supplying an alkylating agent and a basic compound in order to control the reaction temperature and the pH of the reaction solution to be constant.

In addition, hydroxycarbamic acid ester (II) as an intermediate may be isolated on the way, or two reactions, carbamoylation and dialkylation, may be continuously carried out using the same reactor without isolating said intermediate. In consideration of reaction time and cost for extraction solvent, it is preferred that the two reactions are carried out using the same reactor without performing the isolation on the way.

The reaction temperature range at the time of carbamoylation or dialkylation is generally from −20° to 80° C., preferably from −10° to 40° C., more preferably from 0° to 25° C.

The pH range of the reaction solution at this time is generally 7–14, preferably 11–14, more preferably 12–14.

Particularly, the combination of the reaction temperature of 5°±5° C. with the reaction solution pH of 12–13 is optimum in case of industrially preparing the aimed product because not only the yield is high but also the reaction temperature and the reaction solution pH can be easily controlled.

The reaction pressure is generally at atmospheric pressure or higher. In case that an alkylating agent vaporizes under the reaction conditions, it is required to carry out the reaction under pressure.

As examples of N,O-dialkylhydroxycarbamic acid ester (III) to be obtained as above, N,O-dimethylhydroxycarbamic acid ester such as methyl N,O-dimethylhydroxycarbamate, ethyl N,O-dimethylhydroxycarbamate, propyl N,O-dimethylhydroxycarbamate, butyl N,O-dimethylhydroxycarbamate, etc.; N,O-diethyl hydroxycarbamic acid ester such as methyl N,O-diethylhydroxycarbamate, ethyl N,O-diethylhydroxycarbamate, propyl N,O-diethylhydroxycarbamate, butyl N,O-diethylhydroxycarbamate, etc.; N,O-dipropylhydroxycarbamic acid ester such as methyl N,O-dipropylhydroxycarbamate, ethyl N,O-dipropylhydroxycarbamate, propyl N,O-dipropylhydroxycarbamate, butyl N,O-dipropylhydroxycarbamate, etc.; and N,O-dibutylhydroxycarbamic acid ester such as methyl N,O-dibutylhydroxycarbamate, ethyl N,O-dibutylhydroxycarbamate, propyl N,O-dibutylhydroxycarbamate, butyl N,O-dibutylhydroxycarbamate, etc. can be enumerated, among which methyl N,O-dimethylhydroxycarbamate is particularly suitable.

According to the present process for preparing N,O-dialkylhydroxycarbamic acid ester, dihydrocarbyl carbonate (I) is not only difficult to be hydrolyzed but also unreactive with hydroxy group of hydroxycarbamic acid ester as an intermediate. Therefore, N,O-dialkylhydroxycarbamic acid ester as the aimed product can be obtained in high yields.

Although it is possible to carry out the recovery of the above-mentioned N,O-dialkylhydroxycarbamic acid ester (III) by extraction with an organic solvent such as chloroform, methylene chloride, ethylene dichloride or the like, the present inventors found in the course of their variously studying recovery and purification steps of the N,O-dialkylhydroxycarbamic acid ester (III) that said ester had an azeotropic point with water existing in the reaction system and that unreacted starting materials or O-alkylhydroxycarbamic acid ester (IV) as impurities did not become contained in the azeotropic composition when the ester (III) as the aimed product was directly distilled.

Hereinafter, the present process for recovering N,O-dialkylhydroxycarbamic acid ester will be detailed.

A reaction mixture to be subjected to the present method, as previously mentioned, for example, in the present process for preparing N,O-dialkylhydroxycarbamic acid ester, is obtained by firstly reacting a hydroxylamine salt such as hydroxylamine sulfate or the like with dihydrocarbyl carbonate in the presence of a basic compound such as sodium hydroxide or the like and subsequently reacting the reaction product with an alkylating agent such as dimethyl sulfate, methyl bromide or the like, and it contains N,O-dialkylhydroxycarbamic acid ester. Hitherto, N,O-dialkylhydroxycarbamic acid ester has been isolated by adding an organic solvent such as chloroform, methylene chloride, ethylene dichloride or the like to this reaction mixture to extract said ester and subsequently fractionally distilling the same.

The present invention includes a process for recovering N,O-dialkylhydroxycarbamic acid ester comprising azeotropically distilling N,O-dialkylhydroxycarbamic acid ester with water to recover said ester, without extracting the ester from the reaction mixture using an organic solvent as described above.

The present invention also include a process for recovering N,O-dialkylhydroxycarbamic acid ester comprising azeotropically distilling N,O-dialkylhydroxycarbamic acid ester with water from a solution containing inorganic salts such as sodium sulfate, sodium chloride, etc. as are byproducts to be formed in a step of preparing N,O-dialkylhydroxycarbamic acid ester, an unreacted agent and O-alkylhydroxycarbamic acid ester to be formed as impurities to selectively and easily purifying and distilling said ester.

Hereinafter, the process for recovery according to the present invention will be described more specifically. However, the scope of this invention is nowise restricted to the following conditions.

N,O-dialkylhydroxycarbamic acid ester can be prepared according, for example, to the present process for preparing thereof described above.

The present invention is characterized by making N,O-dialkylhydroxycarbamic acid ester form an azeotrope with water from a solution in its preparing step and subsequently distilling N,O-dialkylhydroxycarbamic acid ester. The quantity of water necessary to form an azeotrope is generally the compositional quantity of an azeotrope of water and N,O-dialkylhydroxycarbamic acid ester. That is, under atmospheric or reduced pressure distillation conditions, the quantity of water by weight ratio is generally 1.0 or more, preferably 1.0–1.1 per N,O-dialkylhydroxycarbamic acid ester.

The supply of water to be used for forming the above azeotrope is generally carried out by adding a quantity necessary for azeotropic composition at the time of distillation. However, water which has already existed in the mixture to be subjected may be used. In addition, a mixture generally is a homogeneous system containing organic compounds such as alcohol and the like and inorganic compounds. However, it does not matter if the mixture is a heterogenous system containing other organic and inorganic compounds.

As a distillation apparatus of the above azeotrope composition, it is generally desirable to use an apparatus carrying a distillation column having a fractionally distilling function such as an Oldershow distillation column or the like, that is, an apparatus which enables selective recovery of azeotropic compositions alone. However, it is possible to use a batch system apparatus and a continuous system apparatus each having a function of simultaneously recovering other compounds and azeotropic compositions.

Pressure conditions in the above distillation may be any of atmospheric pressure, pressurization or reduced pressure. Generally, atmospheric pressure or reduced pressure is adopted. The pressure range is preferably 1–760 mmHg, more preferably 10–250 mmHg. The distillation is generally carried out at a boiling point temperature where an azeotrope is formed at a set pressure. The distillation temperature, though it ranges preferably from 20° to 160° C., more preferably from 30° to 80° C., may exceed a boiling point temperature where an azeotrope is formed at a set pressure.

According to the present recovery method described above, it becomes possible to selectively recover N,O-dialkylhydroxycarbamic acid ester more easily and safely than the conventional methods by azeotropically distilling said ester with water, without extracting the ester with an organic solvent.

Although N,O-dialkylhydroxylamine (V) can be prepared by hydrolyzing N,O-dialkylhydroxycarbamic acid ester (III) with acids such as hydrochloric acid or an sulfuric acid, free anhydrous N,O-dialkylhydroxylamine can be obtained without forming N,O-dialkylhydroxylamine salt by carrying out hydrolysis using a catalystic quantity of an alkali instead of acids according to an industrial method.

Hereinafter, the present process for preparing N,O-dialkylhydroxylamine will be detailed.

As N,O-dialkylhydroxycarbamic acid ester (III) in the present preparing process, compounds given as the products in the previously described present process for preparing N,O-dialkylhydroxycarbamic acid ester are preferable, among which methyl N,O-dimethylhydroxycarbamate is particularly suitable.

As examples of a process for preparing N,O-dialkylhydroxycarbamic acid ester as an intermediate to be used in the present preparing process, a process disclosed in West German Patent Application Laid-open No. 3,245,503 comprising reacting hydroxylamine with butyl chloroformate to obtain butyl hydroxycarbamate and subsequently dimethylating this product with dimethyl sulfate to prepare butyl N,O-dimethylhydroxycarbamate; a process disclosed in Org. Prep. Proceed. [Vol. 19, P. 74 (1987)] comprising using ethyl chloroformate as a reaction agent to prepare ethyl N,O-dimethylhydroxycarbamate; and the above-mentioned present process for preparing N,O-dialkylhydroxycarbamic acid ester comprising reacting hydroxylamine with dihydrocarbyl carbonate to obtain hydroxycarbamic acid ester and subsequently dialkylating this product using an alkylating agent to prepare N,O-dialkylhydroxycarbamic acid ester can be enumerated.

As examples of an alkali to be used for hydrolysis in the present preparing process, hydroxides, carbonates, etc. of alkali metals such as lithium, sodium, potassium, etc.; hydroxides, carbonates, etc. of alkaline earth metals such as magnesium, calcium, barium, etc.; organic strong bases such as 4-dimethylaminopyridine (4-DMAP), 1,8-diazabicyclo [5.4.0]-7-undecen (DBU), etc.; and weakly basic ion exchange resins such as Amberlite-93 (registered trademark), Amberlist-21 (registered trademark), etc. can be enumerated, among which hydroxides or carbonates of alkali metals such as lithium, sodium, postassium, etc. are preferable.

In the present preparing process, the quantity of an alkali to be used is generally 0.1–10 mole, preferably 0.5–2 moles per mole of N,O-dialkylhydroxycarbamic acid ester (III).

As a reaction solvent, both an aqueous solution, generally water alone or a hydrous solvent, i.e. a mixed solvent of water with a water-soluble organic solvent (e.g.,alcohols such as methanol, ethanol, etc.; cyclic ether such as tetrahydrofuran, dioxane, etc.) may be used. The quantity of water to be used is generally 1–100 parts by weight, preferably 1.5–10 parts by weight per part by weight of N,O-dialkylhydroxycarbamic acid ester (III). The quantity of organic solvent to be mixed with water is generally 0.1–10 parts by weight per part by weight of water.

The reaction is generally carried out at 25°–120° C. for 1–20 hours preferably at 60°–100° C. for 3–10 hours.

As the reaction proceeds, N,O-dialkylhydroxylamine (V) as a product and an alcohol derived from an ester such as methanol, ethanol, propanol, butanol or the like are distilled out, followed by cooling and recovering this mixture. The obtained mixture of N,O-dialkylhydroxylamine (V) and an alcohol is separated by an ordinary distillation method using a fractionating column to give the aimed N,O-dialkylhydroxylamine (V).

According to the present preparing process described above, it becomes possible to provide free, anhydrous N,O-dialkylhydroxylamine according to an industrial process, without forming a N,O-dialkylhydroxylamine salt.

In case of hydrolyzing N,O-dialkylhydroxycarbamic acid ester (III) with hydrochloric acid to form N,O-dialkylhydroxylamine (V), O-alkylhydroxylamine hydrochloride that is also produced as by-product is contained in N,O-dialkylhydroxylamine hydrochloride. O-alkylhydroxylamine hydrochloride is converted into O-alkyl aldoxime or O-alkylketoxime, which can be recovered easily, with an aldehyde of $C_2-C_8$ or a ketone of $C_2-C_8$ and subsequently the hydrochloride of N,O-dialkylhydroxylamine (V) is separated from the system. Whereby, the hydrochloride of N,O-dialkylhydroxylamine (V) can be purified safely and easily.

Hereinafter the present process for purifying N,O-dialkylhydroxylamine hydrochloride will be detailed.

Alkyl groups in the above N,O-dialkylhydroxylamine hydrochloride and O-alkylhydroxylamine hydrochloride are lower alkyl groups represented by $R^2$ in the above formulae (III)–(V), that is, alkyl groups of $C_1-C_4$, which, for example, include a methyl group, an ethyl group, a n-propyl group, an isopropyl group, a n-butyl group, an isobutyl group, a sec-butyl group and tert-butyl group.

As examples of N,O-dialkylhydroxylamine hydrochloride, N,O-dimethylhydroxylamine hydrochloride, N,O-diethylhydroxylamine hydrochloride, N,O-di-n-propylhydroxylamine hydrochloride, N,O-diisopropylhydroxylamine hydrochloride, N,O-di-n-butylhydroxylamine hydrochloride, N,O-di-isobutylhydroxylamine hydrochloride, N,O-di-sec-butylhydroxylamine hydrochloride, N,O-di-tert-butylhydroxylamine hydrochloride, etc. can be enumerated. And, as examples of O-alkylhydroxylamine hydrochloride, O-methylhydroxylamine hydrochloride, O-ethylhydroxylamine hydrochloride, O-n-propylhydroxylamine hydrochloride, O-isopropylhydroxylamine hydrochloride, O-n-butylhydroxylamine hydrochloride, O-isobutylhydroxylamine hydrochloride, O-sec-butylhydroxylamine hydrochloride, O-tert-butylhydroxylamine hydrochloride, etc. can be enumerated.

An aqueous solution or a hydrochloric acid solution of N,O-dialkylhydroxylamine hydrochloride containing O-alkylhydroxylamine hydrochloride can be obtained according to methods disclosed, for example, in West German Patent Application Laid-open No. 3,245,503 and Org. Prep. Proced. [Vol. 19, p. 75 (1987)], etc., that is, a method comprising hydrolyzing N,O-dimethylhydroxycarbamic acid ester with concentrated hydrochloric acid. These solution contains ethanol and butanol. In addition, it can be also obtained by adding N,O-dimethylhydroxylamine containing O-methylhydroxylamine, which is obtained according to a method disclosed in the specification of U.S. Pat. No. 3,336,731, to a hydrochloric acid solution or an organic solvent such as alcohol or the like which contains hydrochloric acid. As described above, these solutions of N,O-dialkylhydroxylamine hydrochloride containing O-alkylhydroxylamine hydrochloride may be aqueous solutions; organic solvents such as alcohol, hydrocarbon, ether, etc.; or mixed solvents of these.

The state of said solution, thought it may be heterogeneous, is desirably homogeneous.

As examples of aldehyde and ketone of $C_2-C_8$, aliphatic aldehydes such as acetaldehyde, propionaldehyde, butylaldehyde, isobutylaldehyde, pivalaldehyde, valeraldehyde (pentanal), isovaleraldehyde, caproaldehyde (hexanal), heptanal, octanal, chloral, etc.; alicyclic aldehydes such as cyclohexanecarbaldehyde, methyl cyclohexanecarbaldehyde, etc.; unsaturated alicyclic aldehydes such as cyclohexenecarbaldehyde, etc.; aromatic aldehydes such as benzaldehyde, tolaldehyde, etc.; aliphatic ketones such as acetone, methyl ethyl ketone, 2-pentanone, 3-pentanone, methyl isopropyl ketone, 2-hexanone, 3-hexanone, methyl isobutyl ketone, ethyl isopropyl ketone, 2-heptanone, 3-heptanone, 4-heptanone, 2-octanone, etc.; cyclic ketones such as cyclopentanone, cyclohexanone, methyl cyclohexanone, cycloheptanone, cyclooctanone, etc.; unsaturated cyclic ketones such as cyclohexenone, methyl cyclohexenone, cycloheptenone, cyclooctenone, etc.; and an aromatic ketone such as acetophenone can be enumerated.

The quantity of aldehyde or ketone to be added is necessarily 1 equivalent or more, preferably 1–10 equivalents to the contained O-alkylhydroxylamine hydrochloride.

The reaction temperature is generally 0°–150° C., preferably 20°–100° C. The reaction pressure is not lower than atmospheric pressure. The reaction time, though it depends upon the reaction temperature and such, is generally 0.1–48 hours, preferably 0.5–24 hours.

Here, a process for separating N,O-dialkylhydroxylamine hydrochloride from the reaction system is described.

The hydrochloride of N,O-dialkylhydroxylamine can be separated from the system by distilling O-alkyl aldoxime or O-alkyl ketoxime away together with a solvent used. As an example of this process, the process disclosed in Org. Prep. Proced. [Vol. 19, P. 75 (1987)] can be enumerated. In addition, N,O-dialkylhydroxylamine hydrochloride may be separated from the system after recovering O-alkyl aldoxime or O-alkyl ketoxime previously by distillation, extraction or the like.

O-alkyl oxime converted from O-alkylhydroxylamine in the present method, for example, includes O-methyl acetaldehydeoxime (boiling point, 47° C.) to be obtained by addition of acetaldehyde, O-methyl acetoneoxime (boiling point, 72° C.) to be obtained by addition of acetone, etc. Since O-alkyl oximes to be formed according to the present invention have boiling points over room temperature as above, they can be recovered easily.

According to the present purification process described above, it becomes possible to safely carry out the purification of N,O-dialkylhydroxylamine in which O-alkylhydroxylamine hydrochloride is removed from N,O-dialkylhydroxylamine hydrochloride, as was a problem of safety in the conventional methods. In addition, it becomes possible to easily recover O-alkyl oxime after the removal.

Incidentally, in the case of azeotropically distilling a crude product of N,O-dialkylhydroxycarbamic acid ester (III) with water according to the present recovery process described above, O-alkylhydroxycarbamic acid ester existing as impurities can be removed almost completely and thus N,O-dialkylhydroxylamine or its salt does not contaminated by O-alkylhydroxylamine or its salt after hydrolyzing the resulting product. Therefore, the above purification procedures are unnecessary.

In the case of hydrolyzing N,O-dialkylhydroxycarbamic acid ester (III) with hydrochloric acid to form N,O-dialkylhydroxylamine hydrochloride(V), N,O-dialkylhydroxylamine hydrochloride can be obtained simply and easily as a crystal by (i) adding benzene or alkylated benzene to an aqueous solution containing N,O-dialkylhydroxylamine hydrochloride to azeotropically remove water or a hydrochloric acid solution and subsequently (ii) adding alcohol to the resulting solution. In addition, a solvent used can be recovered in high yields.

Hereinafter, the present process for separating N,O-dialkylhydroxylamine hydrochloride will be detailed.

Alkyl groups in the above N,O-dialkylhydroxylamine hydrochloride are lower alkyl groups represented by $R^2$ in the above formulae (III)–(V), that is, alkyl groups of $C_1-C_4$, which, for example, include a methyl group, an ethyl group, a n-propyl group, an isopropyl group, a n-butyl group, an isobutyl group, a sec-butyl group and tert-butyl group.

As N,O-dialkylhydroxycarbamie acid ester (III) in the present preparing process, the same compounds as given in the previously described in the present process for purifying N,O-dialkylhydroxylamine hydrochloride can be enumerated.

In the present separation process, the aqueous solution containing N,O-dialkylhydroxylamine hydrochloride means an water containing N,O-dialkylhydroxylamine hydrochloride or a solution prepared by dissolving N,O-dialkylhydroxylamine hydrochloride in a solution containing hydrochloric acid and water.

Aqueous solutions containing N,O-dialkylhydroxylamine hydrochloride can be obtained according, for example, to the methods disclosed in the specification of West German Patent Application Laid-open No. 3,245,503, *Org. Prep. Proced.* [Vol 19, P. 75 (1987)], etc. described above, that is, by hydrolyzing N,O-dialkylhydroxycarbamic acid ester with concentrated hydrochloric acid, and these solutions contain alcohols such as butanol, ethanol, etc. These solutions can be also given by adding N,O-dimethylhydroxylamine obtained according to the methods disclosed in the specification of U.S. Pat. No. 3,336,731, etc. to a hydrochloric acid solution.

These aqueous solutions containing N,O-dialkylhydroxylamine hydrochloride may be mixed with organic solvents such as alcohol and the like.

In the present separation process, it is desirable that starting materials are previously made as free as possible from water or a hydrochloric acid solution in order to improve productivity. The removal of water or a hydrochloric acid solution may be carried out both under atmospheric pressure or reduced pressure. That is, the pressure at this time ranges from 5 mmHg to atmospheric pressure. The treatment temperature is required to be a temperature at which the boiling takes place at a set pressure.

In order to azeotropically remove water or a hydrochloric acid solution, benzene or alkylated benzene is used.

Alkylated benzene to be used here is preferably benzene substituted by 1 to 3 alkyl groups of $C_1$–$C_3$.

As preferable examples of the alkylated benzene, toluene, xylene, ethylbenzene, cumene, trimethylbenzene, ethyl toluene, cymene, etc. can be enumerated, among which toluene and xylene are particularly desirable from the viewpoint of safety and price.

Alcohol to be added after the azeotropic removal of water or a hydrochloric acid solution is preferably alcohol of $C_1$–$C_6$. As preferable examples of said alcohol, methanol, ethanol, propanol, 2-propanol, butanol, 2-butanol, t-butanol, 2-hexanol, cyclohexanol, etc. can be enumerated, among which methanol, ethanol, propanol and 2-propanol are particularly desirable from the viewpoint of price and easiness of removal at the time of drying.

Alcohols to be added may contain other organic solvents such as aromatic hydrocarbon, etc. For example, when toluene was used as an azeotropic dehydrating agent and 2-propanol is added, the filtrate after filtering crystals out becomes a mixture of toluene and 2-propanol. Although 2-propanol is recovered as a mixed solvent with toluene because it forms an azeotrope with toluene, there is no problem at all if this used as it is.

Hereinafter, conditions such as the quantity of a starting material to be used and the like in order to put the present separation method in practice will be described.

Firstly, the quantity of a starting material to be used will be described.

The quantity of benzene or alkylated benzene to be used at the time of azeotropically removing water or a hydrochloric acid solution is generally 0.1–30 times by weight, preferably 1–10 times by weight based on a solution of N,O-dialkylhydroxylamine hydrochloride.

The quantity of alcohol to be added is generally 0.01–20 times by weight, preferably 0.05–10 times by weight based on benzene or alkylated benzene.

Next, conditions such as treatment pressure, treatment temperature, etc. will be described.

The pressure at the time of adding benzene or alkylated benzene to azeotropically remove water or a hydrochloric acid solution generally ranges from 10 mmHg to atmospheric pressure. The treatment temperature is required to be a temperature causing boiling under a set pressure.

In the next step, alcohol is added to carry out crystallization, dissolution of crystals for recrystallization or reslurrying. At this time, the treatment temperature is generally 20°–150° C., preferably 50°–120° C. and the treatment pressure is not lower than atmospheric pressure. Then, the temperature is lowered to −20°–60° C., crystals are filtered off and dried.

In addition, as described in Example 25, the moisture content of the filtrate after recrystallization is 4,500 ppm. Because the moisture content of the filtrate is such very low as above in the the present, it is possible that, if alcohol which forms an azeotrope with water is used, the alcohol can be recovered in high yields by procedures such as distillation and the like.

Furthermore, when toluene is used as an agent for azeotropic removal and 2-propanol is added, the filtrate after filtering crystals becomes a mixed solvent of toluene and 2-propanol, as described above. Although 2-propanol is recovered as a mixed solvent with toluene because it forms an azeotrope with toluene, there is no problem at all if this is used as it it as described in Example 26.

According to the present separation process, not only the removal of water or a hydrochloric acid solution, which has been difficult according to the conventional separation methods, becomes easy but also it becomes possible to recover a solvent used for an agent for azeotropic removal and a solvent added for crystallization, recrystallization or reslurrying in high yields.

EXAMPLES

Hereinafter, the present invention will be described more specifically, referring to examples, comparative examples and referential examples. However, the scope of the present invention will nowise restricted to the examples.

Example 1

A stirrer piece was placed in a 200-ml four-neck flask equipped with an electrode of a pH meter, a thermometer, an injector and a supply pipe of a feed pump. Then, 8.2 g (95 mmol) of 95% hydroxylamine sulfate (produced by Wako Junyaku Co., Ltd.) and 25 ml of water were added to this flask, followed by cooling the flask to have an internal temperature of 5° C. In an atmosphere of nitrogen, a 50% sodium hydroxide solution was so dropwise added to the above solution by the injector that the pH of the reaction solution reaches 13. Maintaining the internal temperature at 5° C. and the pH of the reaction solution at 13, 10 g (108 mmol) of dimethyl carbonate (produced by Wako Junyaku Co., Ltd.) and a 50% sodium hydroxide solution were simultaneously supplied into the flask respectively with the injector and the feed pump over a period of 40 minutes. After the completion of supply, the mixture was stirred for 2 hours under the above conditions. Thereafter, maintaining the reaction temperature at 5° C. and the pH of the reaction solution at 13, 27.8g (209 mmol) of 95% dimethyl sulfate (produced by Wako Junyaku Co., Ltd.) and a 50% sodium hydroxide solution were simultaneously supplied into the flask respectively with the feed pipe and the injector over a period of 1 hour. After the completion of supply, the mixture was stirred for 3 hours under the above conditions. Then, chloroform was added to the reaction solution to extract methyl N,O-dimethylhydroxycarbamate. As a result of quantitatively analyze the extract by gas chromatography, 11.0 g (yield, 97%) of methyl N,O-dimethylhydroxycarbamate was formed.

Examples 2–8

Reactions were carried out under the same conditions as in Example 1, except that only the pH of the reaction solution was changed. Results of the experiments were given in Table 1.

TABLE 1

| No. of Example | pH in Carbamoylation | pH in Dimethylation | Yield (%) |
| --- | --- | --- | --- |
| 2 | 12.5 | 12.5 | 98 |
| 3 | 12 | 12 | 90 |
| 4 | 12 | 13 | 94 |
| 5 | 13 | 12 | 94 |
| 6 | 13.5 | 13.5 | 92 |
| 7 | 14 | 13 | 91 |
| 8 | 14 | 14 | 84 |

Example 9

4.55 g (50 mmol) of methyl hydroxycarbamate, which had been isolated by adjusting the reaction solution after the carbamoylation in Example 1 to pH 7, evaporating the reaction solution to dryness, extracting the dried product with ethyl acetate and then subjecting to column chromatography, and 15 ml of water were loaded into the same reaction device as in Example 1, followed by cooling the internal temperature of the device to 5° C. In an atmosphere of nitrogen, a 50% sodium hydroxide solution was dropwise added to the mixture from an injector so as to adjust the the reaction solution to pH13. Maintaining the internal temperature at 5° C. and the pH of the reaction solution at 13, 13.9 g (105 mmol) of 95% dimethyl sulfate (produced by Wako Junyaku Co., Ltd.) and a 50% sodium hydroxide solution were simultaneously supplied to the device respectively with the feed pump and the injector over a period of 1 hour. After the completion of supply, the mixture was stirred for 5 more hours under the above conditions. Then, chloroform was added to the reaction solution to extract methyl N,O-dimethylhydroxycarbamate. As a result of quantitatively analyze the extract by gas chromatography, 5.2 g (yield, 87%) of methyl N,O-dimethylhydroxycarbamate was formed.

Comparative Example 1

A stirrer piece was placed in a 50-ml four-neck flask equipped with a thermometer and an injector. Then, 1.67 g. (20 mmol) of 95% hydroxylamine sulfate (produced by Wako Junyaku Co., Ltd.) and 5 ml of water were added to this flask, followed by cooling the flask to have an internal temperature of 5° C. In an atmosphere of nitrogen, 2.12 g (22 mmol) of 98% methyl chloroformate was added to the above solution, followed by dropping 6.2 ml of a 10N sodium hydroxide solution from the injector over a period of 1 hour with maintaining the reaction temperature at 8° C. or lower. Maintaining the internal temperature within the range of 2°–5° C., the mixture was stirred for 3 more hours. Thereafter, 5.84 g (44 mmol) of 95% dimethyl sulfate (produced by Wako Junyaku Co., Ltd.) was added to the reaction solution, followed by dropping 2.4 ml of 10N sodium hydroxide solution using the injector over a period of 30 minutes. After the completion of supply, the reaction temperature was raised to 15°–20° C., at which the mixture was stirred for 3 hours. Thereafter, the reaction solution was subjected to quantitative analysis by liquid chromatography. As a result of repeating the same reaction as above twice, 0.87 g (yield, 37%) and 1.15 g (yield, 47%) of methyl N,O-dimethylhydroxycarbamate were formed respectively.

Example 10

The reaction was carried out under quite the same conditions as in Comparative Example 1, except that dimethyl carbonate was used instead of methyl chloroformate and the quantity of a 10N sodium hydroxide solution to be dropped after the addition of dimethyl carbonate was changed to 4 ml. As the result, the yield of methyl N,O-dimethylhydroxycarbamate was 72%.

Referential Example 1

A 50-ml four-neck flask equipped with a thermometer and two injectors was loaded with 1.82 g (20 mmol) of methyl hydroxycarbamate and 6 m of water. Then, 0.77 ml (10 mmol) of 98% methyl chloroformate and 1 m (10 mmol) of a 10N sodium hydroxide solution were simultaneously dropped into the flask over a period of 20 minutes from the injectors with maintaining the reaction temperature at 5° C. Maintaining the internal temperature at 5° C., the mixture was stirred for 1 more hour. As a result of qualitatively analyzing the reaction mixture by liquid chromatography, it was found that methyl O-methoxycarbonylhydroxycarbamate was formed. The peak area ratio of methyl hydroxycarbamate as the raw material to methyl O-methoxycarbonylhydroxycarbamate in liquid chromatography was 62:35.

Referential Example 2

The reaction was carried out under quite the same condition as in Referential Example 1, except that dimethyl carbonate was used instead of methyl chloroformate. As the result, methyl O-methoxycarbonylhydroxycarbamate was not formed at all.

Example 11

41.03 g (0.485 mol) of 95% hydroxylamine sulfate and 125 m of water was added to a flask, followed by cooling the internal temperature of the flask to 5° C. In an atmosphere of nitrogen, a 50% sodium hydroxide solution was so dropped into the above solution from a dropping funnel that the pH of the reaction solution reached 12. Then, maintaining the internal temperature at 5° C. and the pH of the reaction solution within the range of 12–13, 49.59 (0.52 mol) of 98% dimethyl carbonate and a 50% sodium hydroxide solution were simultaneously supplied into the flask respectively from the dropping funnels over a period of 40 minutes. After the completion of supply, the mixture was stirred for 30 minutes under the same conditions. Thereafter, maintaining the reaction temperature within the range of 5–8° C. and the pH of the reaction solution within the range of 12–13, 139.0 g (1.05 mol) of 95% dimethyl sulfate and a 50% sodium hydroxide solution were simultaneously supplied into the flask respectively from dropping funnels over a period of 1.5 hours. After the completion of supply, the mixture was stirred for 3 hours under the same conditions. Then, the reaction temperature was raised to 50° C., and the reaction solution was stirred for 30 minutes with maintaining the pH thereof at 7.3 by dropping a saturated sodium hydrogencarbonate solution to decompose excessive dimethyl sulfate. After cooling to room temperature, the reaction solution was quantitatively analyzed by gas chromatography to find that 54.9 g (yield, 95%) of methyl N,O-dimethylhydroxycarbamate was formed. Then, a five-stage Oldershow distillation column was attached to the flask to distill the reaction solution under a reduced pressure of 50–80 mmHg and at a boiling point of 40°–50° C. Whereby, 181.3 g (purity, 29.0%; isolation yield, 92.5%) of an azeotropic distillate with water containing methanol and methyl N,O-dimethylhydroxycarbamate was obtained. N,O-dimethylhydroxylamine hydrochloride as the final product can be obtained by adding hydrochloric acid to this azeotropic distillate to hydrolyze the same and then evaporating the hydrolysate to dryness.

Example 12

The reaction was carried out in the same manner as in Example 11, except that the distillation was carried out at an atmospheric pressure and at a boiling point of 90°–105° C. instead of a reduced pressure of 50–80 mmHg and a boiling point of 40°–50° C. As the result, 183.1 g (purity, 24%; isolation yield, 77%) of an azeotropic distillate with water containing methanol and methyl N,O-dimethylhydroxycarbamate was obtained.

Referential Examples 3–6

After cooling a reaction mixture containing 109.7 g of methyl N,O-dimethylhydroxycarbamate obtained under the same conditions as in Example 11 except that the quantity of hydroxylamine sulfate used was 0.95 mol to room temperature, 500 m of methylene chloride was added thereto, stirred for 30 minutes and then transferred to a separatory funnel. After leaving the funnel stationarily for 30 minutes, the oily layer (the lower layer) was extracted. After repeating the extraction in the same manner using 500 ml of methylene chloride, the extracted oily layers were combined and washed with 100 ml of water. About 500 ml portion of the washed oily layer was loaded into a 1—1 round-bottom flask equipped with a 60-mm Vigraux fractional column and then heated in a water bath (47°–52° C.) to distill methylene chloride away. Using a supply pipe, the remaining washed oily layer was continuously fed to the column to similarly distill methylene chloride away. The concentrate was transferred to a 300-ml round-bottom flask equipped with a five-stage Oldershow distillation column and superfractionated there to give 108.7 g (purity, 95.2%) of methyl N,O-dimethylhydroxycarbamate as a distillate. The total yield was 91%, and the boiling point was 135°–144° C.

Water each having a ratio by weight given in Table 2 was added to 10.0 g of methyl N,O-dimethylhydroxycarbamate obtained according to the above method, and each solution was distilled using a five-stage Oldershow distillation column. As a result of quantitatively analyzing the distillates by gas chromatography, the results given in Table 2 were obtained.

TABLE 2

| Referential Example No. | Loading Composition N,O-dimethylhydroxy-carbamate:Water (Ratio by Weight) | Pressure (mmHg) | Distillation Temperature (°C.) | Distillate Composition N,O-dimethylhydroxy-carbamate:Water (Ratio by Weight) |
|---|---|---|---|---|
| 3 | 1:0 | 760 | 144 | 100:0 |
| 4 | 1:1 | 760 | 96 | 49:51 |
| 5 | 1:5 | 760 | 97 | 47:53 |
| 6 | 1:5 | 80 | 41 | 45:55 |

Example 13

4.0 g of a 50% sodium hydroxide solution (the molar ratio to methyl N,O-dimethylhydroxycarbamate as NaOH, 0.5) was added to a mixture consisting of 11.9 g (0.1 mol) of methyl N,O-dimethylhydroxycarbamate, 22.2 g of water and 5.6 g of methanol, followed by reacting at 75°–90° C. for 5 hours. As the reaction proceeded, N,O-dimethylhydroxylamine and methanol began to distill from the upper end of a reactor and were recovered in a receiving device cooled to −20° C. This distillate contained 6.1 g of N,O-dimethylhydroxylamine and 6.1 g of methanol. As the result, the conversion ratio of methyl N,O-dimethylhydroxycarbamate was 100%, and the selectivity to N,O-dimethylhydroxylamine was 100%.

Example 14

The reaction was carried out in the same manner as in Example 13, except that the quantity of a 50% sodium hydroxide to be used was 16.0 g. As the result, the conversion ratio of methyl N,O-dimethylhydroxycarbamate was 100%, and the selectivity to N,O-dimethylhydroxylamine was 100%.

Examples 15–19

Reactions were carried out under the reaction conditions prescribed in Table 3 using alkalis other than sodium hydroxide used in Example 13. The results were given in Table 3.

TABLE 3

| Example No. | Alkalis Kind | Alkalis Quantity used | Temperature (°C.) | Time (Hr) | Conversion Ratio (%) | Selectivity (%) |
|---|---|---|---|---|---|---|
| 15 | NaHCO$_2$ | 2* | 100 | 5 | 95 | 100 |

TABLE 3-continued

| Example No. | Alkalis Kind | Alkalis Quantity used | Temperature (°C.) | Time (Hr) | Conversion Ratio (%) | Selectivity (%) |
|---|---|---|---|---|---|---|
| 16 | K$_2$CO$_3$ | 2* | 100 | 10 | 93 | 100 |
| 17 | Ca(OH)$_2$ | 2* | 100 | 5 | 93 | 100 |
| 18 | 4-DMAP | 2* | 100 | 10 | 92 | 100 |
| 19 | IRA-93 (OH type) | 4 (W/W) %** | 100 | 5 | 92 | 100 |

*Alkali/methyl N,O-dimethylhydroxycarbamate (molar ratio)
**Equivalent to double the molar quantity of methyl N,O-dimethylhydroxycarbamate Comparative Example 2

30.3 g (0.3 mol) of concentrated sulfuric acid was added to a mixture consisting of 11.9 g (0.1 mol) of methyl N,O-dimethylhydroxycarbamate, 22.2 g of water and 5.6 g of methanol, followed by reacting at 100°–104° C. for 5 hours. After cooling the reaction solution to room temperature, 50.4 g (0.68 mol) of a 50% sodium hydroxide solution was gradually added thereto. As a result of analyzing the resulting solution after neutralization, the conversion ratio of methyl N,O-dimethylhydroxycarbamate was 100% and the selectivity to N,O-dimethylhydroxylamine was 93%.

Example 20

289 mg of acetaldehyde was added to 14 g of an aqueous solution containing 0.15 g of O-methylhydroxylamine hydrochloride, 2.86 g of N,O-dimethylhydroxylamine hydrochloride and 3 ml of hydrochloric acid, followed by stirring at 25° C. for 12 hours.

After the completion of stirring, a part of the reaction solution was taken out, to which a 50% sodium hydroxide solution was so added that its pH reached 12 or more. As a result of analyzing this reaction solution by gas chromatography, it was found that O-methylhydroxylamine was completely disappeared and that O-methylacetaldehyde oxime was formed. Next, the hydrochloric acid solution and O-methylactaldehyde oxime were removed from this reaction solution using a rotary evaporator. After adding 10 ml of isopropyl alcohol to thus treated reaction solution and repeatedly subjecting the resulting solution to azeotropic distillation 6 times, 2.5 ml of isopropyl alcohol was added to the azeotrope, cooled to 0° C and then filtered to obtain crystals. The obtained crystals were dried under reduced pressure of 1 mmHg or less at room temperature for 24 hours. Whereby, 2.66 g of N,O-dimethylhydroxylamine hydrochloride could be obtained (recovery, 93%). The recovered N,O-dimethylhydroxylamine hydrochloride was dissolved in a small quantity of water, adjusted to have a pH of 12 or more with a 50% sodium hydroxide solution and then analyzed by gas chromatography. As the result, O-methylhydroxylamine was not contained at all.

Example 21

389 mg of benzaldehyde was added to 14 g of an aqueous solution containing 0.15 g of O-methylhydroxylamine hydrochloride, 2.86 g of N,O-dimethylhydroxylamine hydrochloride and 3 m of hydrochloric acid, followed by stirring at 25° C. for 12 hours.

After the completion of stirring, a part of the reaction solution was taken out, to which a 50% sodium hydroxide solution was so added that its pH reached 12 or more. As a result of analyzing this reaction solution by gas chromatography, it was found that O-methylhydroxylamine was completely disappeared. Next, this reaction solution was transferred to a separatory funnel, extracted 3 times with 10 m of diethyl ether to recover unreacted benzaldehyde and O-methylbenzaldehyde oxime. The aqueous layer was transferred to a 100-m round-bottom flask. Thereafter, the same post-treatment as in Example 20 was carried out. Whereby, 2.71 g of N,O-dimethylhydroxylamine hydrochloride could be recovered (recovery, 95%). The recovered N,O-dimethylhydroxylamine hydrochloride was dissolved in a small quantity of water, adjusted to have a pH of 12 or more with a 50% sodium hydroxide solution and then analyzed by gas chromatography. As the result, O-methylhydroxylamine was not contained at all.

Example 22

Using 5.35 g of an aqueous solution containing 57.4 mg of O-methylhydroxylamine hydrochloride, 1.09 g of N,O-dimethylhydroxylamine hydrochloride and 37.6 mg of hydrochloric acid as a raw material, the reaction was carried out in the same manner as in Example 20, except that kind and the quantity of aldehyde and ketone were changed. Thereafter, N,O-dimethylhydroxylamine hydrochloride was isolated according to the method of Example 20, followed by analysis of 0 methylhydroxylamine hydrochloride contained therein. The results were given in Table 4.

Example 23

Using 5.35 g of an aqueous solution containing 57.4 mg of O-methylhydroxylamine hydrochloride, 1.09 g of N,O-dimethylhydroxylamine hydrochloride and 37.6 mg of hydrochloric acid as a raw material, the reaction was carried out in the same manner as in Example 21, except that kind and the quantity of aldehyde and ketone were changed. Thereafter, N,O-dimethylhydroxylamine hydrochloride was isolated according to the method of Example 21, followed by analysis of O-methylhydroxylamine hydrochloride contained therein. The results were given in Table 4.

TABLE 4

| Example No. | Additive (Quantity, mg) | Quantity of O-methylhydroxylamine (mg) |
|---|---|---|
| 22 | Acetone (160)* | 0 |
| 23 | Cyclohexanone (151) | 0 |

*Stirred for 24 hours.

Example 24

32 mg of acetaldehyde was added to 6 g of an aqueous solution containing 11 mg of O-methylhydroxylamine hydrochloride, 0.22 g of N,O-dimethylhydroxylamine hydrochloride and 0.4 g of methanol, followed by reflux under stirring for 2 hours. Thereafter, N,O-dimethylhydroxylamine hydrochloride was isolated according to the method of Example 20. This isolate was dissolved in a small quantity of water, adjusted to pH 12 or more and then analyzed by gas chromatography. As the result, it was found that O-methylhydroxylamine was completely disappeared.

Example 25

From a hydrochloric acid solution of N,O-dimethylhydroxylamine hydrochloride, which was obtained by stirring 11.9 g of methyl N,O-dimethylhydroxycarbamate and 25 ml of concentrated hydrochloric acid under reflux, 18.1 g of hydrochloric acid solution was removed at a bath temperature of 60° C. under a pressure of 25 mmHg. After adding 25 m of toluene here, azeotropic removal was carried out under atmospheric pressure. After continuing the azeotropic removal until the internal temperature reached 110° C., the resulting solution was cooled to 80° C. Here, 5.5 ml of 2-propanol was added, and the resulting solution was stirred to reslurry under reflux for 1 hour. After cooling the slurry to 20° C., crystals were filtered and dried at room temperature under a pressure of 1 mmHg for 24 hours to obtain 9.56 g (yield, 98%; moisture content, 0.1% or less) of N,O-dimethylhydroxylamine hydrochloride. As a result of determining the moisture content in the filtrate, it was 500 ppm.

Example 26

The isolation of N,O-dimethylhydroxylamine hydrochloride was carried out under quite the same conditions as in Example 25 using the same raw material of said example, except that the quantity of toluene was changed to 17.5 ml and a mixed solvent of toluene and 2-propanol (toluene, 7.5 m; 2-propanol, 5.5 ml) was used instead of 2-propanol. As the result, 9.46 g (yield, 97%) of N,O-dimethylhydroxylamine hydrochloride was obtained.

Example 27–30

The isolation of N,O-dimethylhydroxylamine hydrochloride was carried out under the same conditions as in Example 25 using a hydrochloric acid solution of N,O-dimethylhydroxylamine hydrochloride, which was prepared from 5.95 g of methyl N,O-dimethylhydroxycarbamate and 12.5 ml of concentrated hydrochloric acid, as a raw material, except that kind of alkyl group-substituted benzene, kind of alcohol and conditions for azeotropic removal were changed variously. The results were given in Table 5.

TABLE 5

| Example No. | Alkyl Group-substituted Benzene | Alcohol | Conditions for Azeotropic Removal | Yield (%) |
|---|---|---|---|---|
| 27 | Toluene (20 ml) | 2-Propanol (5 ml) | Under reduced pressure: Bath temperature, 80° C.; 150 mmHg | 93 |
| 28 | Toluene (20 ml) | Ethanol (3 ml) | Under atmospheric pressure | 93 |
| 29 | Xylene (20 ml) | 2-Propanol (5 ml) | Under atmospheric Pressure | 94 |
| 30 | Xylene (20 ml) | 2-Propanol (5 ml) | Under reduced pressure: Bath temperature, 80° C.; 100 mmHg | 94 |

Example 31

A hydrochloric acid solution of N,O-dimethylhydroxylamine hydrochloride was prepared by adding 0.61 g of N,O-dimethylhydroxylamine to 4 ml of concentrated hydrochloric acid. After adding 20 ml of toluene here, azeotropic removal was carried out under atmospheric pressure. After adding 14 m of 2-propanol thereto at 80° C. to prepare a homogeneous solution, this solution was cooled to room temperature, followed by filtration of the formed crystals. The weight of N,O-dimethylhydroxylamine hydrochloride after drying was 0.78 g (yield, 79%).

What is claimed is:

1. A process for preparing N,O-dialkylhydroxycarbamic acid ester represented by the following formula (III)

wherein $R^1$ is a hydrocarbon group, and $R^2$ is a lower alkyl group, comprising reacting hydroxylamine represented by the formula NH2OH or its salt at a temperature of from 0° to 10° C. and at a pH of from 12 to 13 with dihydrocarbyl carbonate represented by the following formula (I)

wherein $R^1$ is as defined above, in the presence of a basic compound to prepare hydroxycarbamic acid ester represented by the following formula (II)

wherein $R^1$ is as defined above, and alkylating the hydroxycarbamic acid ester of formula (II) at a temperature of from 0° to 10° C. and a pH of from 12 to 13 with an alkylating agent in the presence of a basic compound to produce a solution containing the N,O-dialkylhydroxycarbamic acid ester of formula (III).

2. A process according to claim 1, wherein the dihydrocarbyl carbonate is dimethyl carbonate, the hydroxycarbamic acid ester is methyl hydroxycarbamate and the N,O-dialkylhydroxycarbamic acid ester is methyl N,O-dimethylhydroxycarbamate.

3. A process according to claim 1, which further comprises recovering the N,O-dialkylhydroxycarbamic acid ester from the obtained solution containing the ester by azeotropically distilling the solution with water.

4. A process for recovering N,O-dialkylhydroxycarbamic acid ester represented by the following formula (III)

wherein $R^1$ is a hydrocarbon group, and $R^2$ is a lower alkyl group, comprising azeotropically distilling the N,O-dialkylhydroxycarbamic acid ester with water.

5. A process according to claim 4, wherein the N,O-dialkylhydroxycarbamic acid ester is methyl N,O-dimethylhydroxycarbamate.

6. A process for recovering N,O-dialkylhydroxycarbamic acid ester represented by the following formula (III)

wherein $R^1$ is a hydrocarbon group, and $R^2$ is a lower alkyl group, comprising azeotropically distilling N,O-dialkylhydroxycarbamic acid ester with water from a solution containing the N,O-dialkylhydroxycarbamic acid ester and O-alkylhydroxycarbamic acid ester represented by the following formula (IV)

wherein $R^1$ and $R^2$ are as defined above.

7. A process according to claim 6, wherein the N,O-dialkylhydroxycarbamic acid ester is methyl N,O-dimethylhydroxycarbamate.

8. The process according to claim 1 wherein the alkylating agent is dialkylsulfuric acid ester, alkylchloride, alkylbromide or alkyliodide.

9. The process according to claim 1 wherein the alkylating agent is selected from the group consisting of dimethylsulfate, diethylsulfate, methylchloride, ethylchloride, propylchloride, butylchloride, methylbromide, ethylbromide, propylbromide, butylbromide, methyliodide, ethyliodide, propyliodide and butyliodide.

10. The process of according to claim 9, wherein the basic compound used in the carbamoylation reaction and the basic compound used in the alkylation reaction are, independently, selected from the group consisting of hydroxides of alkali metals, hydroxides of alkaline earth metals, hydrogencarbonates of alkali metals, carbonates of alkali metals, carbonates of alkaline earth metals, and aluminate compounds.

11. The process according to claim 10 wherein the basic compound is selected from the group consisting of sodium hydroxide, potassium hydroxide, lithium hydroxide, cesium hydroxide, barium hydroxide, sodium hydrogencarbonate, potassium hydrogen carbonate, sodium carbonate, potassium carbonate, barium carbonate, sodium aluminate and potassium aluminate.

12. The process of claim 1 wherein the basic compound used in the carbamoylation reaction and the basic compound used in the alkylation reaction are, independently, selected from the group consisting of hydroxides of alkali metals, hydroxides, of alkaline earth metals, hydrogencarbonates of alkali metals, carbonates of alkali metals, carbonates of alkaline earth metals, and aluminate compounds.

13. The process of claim 1, wherein the basic compound is selected from group consisting of sodium hydroxide, potassium hydroxide, lithium hydroxide, cesium hydroxide, barium hydroxide, sodium hydrogencarbonate, potassium hydrogencarbonate, sodium carbonate, potassium carbonate, barium carbonate, sodium aluminate and potassium aluminate.

\* \* \* \* \*